United States Patent
Shimmyo

(10) Patent No.: US 7,204,806 B2
(45) Date of Patent: Apr. 17, 2007

(54) METHOD AND APPARATUS FOR OBTAINING CORRECTED INTRAOCULAR PRESSURE VALUES

(76) Inventor: Mitsugu Shimmyo, 345 E. 37th St., Suite 203, New York, NY (US) 10016

( * ) Notice: Subject to any disclaimer, the term of this patent is extended or adjusted under 35 U.S.C. 154(b) by 452 days.

(21) Appl. No.: 10/462,711

(22) Filed: Jun. 17, 2003

(65) Prior Publication Data

US 2004/0260168 A1 Dec. 23, 2004

(51) Int. Cl.
*A61B 3/16* (2006.01)

(52) U.S. Cl. ...................... 600/398; 600/405

(58) Field of Classification Search ........ 600/398–405, 600/561
See application file for complete search history.

(56) References Cited

U.S. PATENT DOCUMENTS

| | | | | |
|---|---|---|---|---|
| 5,474,066 A | * | 12/1995 | Grolman | 600/398 |
| 5,830,139 A | * | 11/1998 | Abreu | 600/405 |
| 6,083,160 A | * | 7/2000 | Lipman | 600/398 |
| 6,083,161 A | * | 7/2000 | O'Donnell, Jr. | 600/405 |
| 6,113,542 A | * | 9/2000 | Hyman et al. | 600/398 |
| 6,419,631 B1 | * | 7/2002 | Luce | 600/401 |

FOREIGN PATENT DOCUMENTS

| | | | |
|---|---|---|---|
| JP | 2003-111732 A | * | 4/2003 |
| WO | WO 03/096888 | * | 11/2003 |
| WO | WO 04/089198 | * | 10/2004 |

OTHER PUBLICATIONS

Shimmyo Mitsugo, M.D., et al.; "Intraocular pressure, Goldmann applanation tension, corneal thickness, and corneal curvature in Caucasians, Asians, Hispanics, and African Americans", American Journal of Ophthalmology, vol. 136, No. 4, 2003, pp. 603-613.*

Mark Johnson, M.D., et al.; "Increased Corneal Thickness Simulating Elevated Intraocular Pressure";Arch Ophthalmol- vol. 96, Apr. 1978, pp. 664-665.

Paul Foster, et al.; "Central Corneal Thickness and Intraocular Pressure in a Mongolian Population";Ophthalmology, vol. 105, No. 6, Jun. 1998; pp. 969-973.

Roger C.W. Wolfs, M.D., et al., "Distribution of Central Corneal Thickness and Its Association With Intraocular Pressure: The Rotterdam Study"; American Journal of Ophthalmology, vol. 123, No. 6, 1997, pp. 767-772.

Harry H. Mark, M.D., "Corneal Curvature in Applanation Tonometry", American Journal of Ophthalmology, Aug. 1973, pp. 223-224.

(Continued)

*Primary Examiner*—Max Hindenburg
*Assistant Examiner*—Michael Apanius
(74) *Attorney, Agent, or Firm*—Buchanan, Ingersoll & Rooney PC

(57) ABSTRACT

The disclosed methods and systems use measured values from applanation tonometry and pachymetry, and corneal curvature values to produce corrected values of intraocular pressure to diagnose and treat pressure related eye diseases.

26 Claims, 2 Drawing Sheets

OTHER PUBLICATIONS

Michael J. Doughty, Ph.D, et al., "Human Corneal Thickness and Its Impact on Intraocular Pressure Measures: A Review and Meta-analysis Approach"; Survey of Ophthalmology, vol. 44, No. 5, Mar.-Apr. 2000, 2000 by Elsevier Science Inc., pp. 367-408.

Thor Eysteinsson, et al., Central corneal thickness, radius of the corneal curvature and intraocular pressure in normal sujbects using non-contact techniques: Reykjavik Eye Study: ACTA Ophthalmologica Scandinavica 2002, ISSN 1395-3907, pp. 11-15.

Ravi Thomas, M.D., et al., The Role of Central Corneal Thickness in the Diagnosis of Glaucoma, Indian Journal of Ophthalmology, 2000, vol. 48, No. 2, pp. 107-111.

Sunil Shah, et al "Relationship between Corneal Thickness and Measured Intraocular Pressure in a General Ophthalmology Clinic"; Ophthalmology, vol. 106, No. 11, Nov. 1999, pp. 2154-2160.

Nicolas Feltgen, et al.; Correlation between central corneal thickness, applanation tonometry, and direct intracarneal IOP readings; Br J Ophthalmol 2001;85:85-87.

Richard F. Brubaker, M.D.;Tonometry and Corneal Thickness, Arch Ophthalmolvol. 117, Jan. 1999, pp. 104-105.

Andrea Hafner, et al., "Durch falsch normale Applanationstonometrie nach Goldmann maaskiertes primar chronisches Offenwinkelglaukom bei extremer Cornea plana", Klin Monatasbl Augenhelikd 2001:218, pp. 621-625; Georg Thieme Verlag Stuttgart—New York, ISSN 0023-2165.

Barry Y. Emara, et al., Clinical Studies, "Central corneal thickness in low-tension glaucoma"; Can J Ophthalmol 1999;34, vol. 6, pp. 319-324.

William A. Argus, M.D., "Ocular Hypertension and Central Corneal Thickness"; Ophthalmology, vol. 102, No. 12, Dec. 1995, pp. 1810-1812.

Marc M. Whitacre, M.D. et al., "The Effect of Corneal Thickness on Applanation Tonometry"; American Journal of Ophthalmology 115:592-596, May 1993.

Richard Stodtmeister, "Applanation tonometry and correction according to corneal thickness"; ACTA Ophthalmologica Scandinavica 1998, ISSN 1395-3907, pp. 319-324.

Rene-Pierre Copt, M.D., et al.; "Corneal Thickness in Ocular Hypertension Primary Open-angle Glaucoma, and Normal Tension Glaucoma"; ARCH Ophthalmol/vol. 117, Jan. 1999.

Leon W. Herndon, M.D., et al.; "Central Corneal Thickness in Normal Glaucomatous, and Ocular Hypertensive Eyes"; ARCH Ophthalmol/vol. 115, Sep. 1997, pp. 1137-1141.

Khaled M. Rashad, M.D., et al.; "Changes in Intraocular Pressure After Laser in situ Keratomileusis"; Journal of Refractive Surgery, vol. 17, Jul./Aug. 2001, pp. 420-427.

Omer F. Recep, M.D., et al.; "Relation between corneal thickness and intraocular pressure measurement by noncontact and applanation tonometry"; J Cataract Refract Surg, vol. 27, Nov. 2001, pp. 1787-1791, 2001 ASCRS and ESCRS, Published by Elsevier Science Inc.

Francis A. La Rosa, M.D., et al.; "Central Corneal Thickness of Caucasians and African Americans in Glaucomatous and Nonglaucomatous Populations"; ARCH Ophthalmol, vol. 119, Jan. 2001, www.Archophthalmol.com.

P. Brusini et al.; "Corneal thickness in glaucoma: an Important parameter?"; ACTA Ophthalmologica Scandinvica 2000, pp. 41-42.

P. Brusini et al., "Quantitative mapping of the retinal thickness at the posterior pole in chronic open angle glaucoma"; ACTA Ophthalmologica Scandinavica 2000, p. 42.

Richard Stodtmeister, et al., Mailbox, "IOP measurement and central corneal thickness", PostScript; www.bjophthalmol.com, pp. 120-121.

A. Fick, "On Measuring the Pressure in the Eye"; pp. 86-90.

Dr. A. Imbert (Montpellier); "Theory of Ophthalmotonometers"; pp. 1-4.

Von H. Goldmann et al., Uber Applanationstonometrie; Ophthalmologica vol. 134,No. 4, pp. 221-242, Oct. 1957.

H. Goldman, "A New Flattening Tonometer" Ophthalmological Clinic Paper, University of Bern, Freiburgstrasse 8 Bern.

H. Goldman et al., "On Applanation Tonometry"; Ophthalmologica, vol. 134, No. 4 (Oct. 1957), pp. 221-241.

Niels Ehlers, et al., "Applanation Tonometry And Central Corneal Thickness"; ACTA Ophthalmologica vol. 53, 1975, pp. 34-43.

Richard Stodtmeister, M.D., "If IOP Measurement is Only an Estimate, Then What?"; Ophthalmology, vol. 108, No. 8, Aug. 2001, pp. 1365-1366.

A C Sobottka Ventura, et al., "Central corneal thickness measurments in patients with normal tension glaucoma, primary open angle glaucoma, pseudoexfoliation glaucoma, or ocular hypertension"; Br J Ophthalmol 2001; 85:792-795, www.bjophthalmol.com.

David C. Herman M.D., et al., "Increased Corneal Thickness in Patients With Ocular Hypertension"; (Reprinted) ARCH Ophthalmol/vol. 119, Mar. 2001, pp. 334-336, 2001 American Medical Association.

Burvenich H., et al., "The Correlation Between IOP Measurement, Central Corneal Thickness and Corneal Curvature"; Bull. Soc. beige Ophtalmol, 276, 23-26, 2000.

Takuya Matsumoto et al., "The Influence of Corneal Thickness and Curvature on the Difference between Intraocular Pressure Measurements Obtained with a Non-contact Tonometer and Those with a Goldman Applanation Tonometer"; pp. 317-321, with Abstract.

Surinder S. Pandav et al.; "Reliability of ProTon and Goldmann ApplanationTonometers in Normal and Postkeratoplasty Eyes"; Ophthalmology, vol. 109, No. 5, May 2002, pp. 979-984, ISSN 0161-6420/2/S: Published by Elsevier Science Inc.

* cited by examiner

METHOD AND APPARATUS FOR OBTAINING CORRECTED INTRAOCULAR PRESSURE VALUES

FIELD OF THE INVENTION

This invention relates to modification and adjustment of currently available methods of determining intraocular pressure (IOP), preferably by obtaining and combining information from applanation tonometry (AT), pachymetry (CCT) and corneal curvature (K) measurements.

BACKGROUND

Accurate measurement of IOP, pressure inside the eye, is extremely important in making the diagnosis of pressure related eye diseases, particularly glaucoma, and in management or making treatment plans such as choosing medications, laser treatment or surgery to control these serious eye diseases.

Applanation tonometry (AT) has long been the standard for clinical measurement of LOP and has generally been accepted to reflect true LOP by generations of ophthalmologists. In fact most ophthalmic literature assumes AT to be LOP. Goldmann's approach is represented by equations based on a modification of principles described by Imbert and by Maklokoff in 1885 and Fick in 1887. Imbert, A., "Theorie sur ophthalmotonometre," Arch Ophthalmol (Paris) 5:3 58–363 (1885); Fick, A., "Ueber Messung des Druckes im Auge" Aech fur Die Gesammte Physiologie des Menschen & der Thiere 42:86–90 (1888). Imbert and Fick analyze the relationship of forces acting on an eye model assumed to be dry and a perfect sphere with an infinitely thin wall. However, the cornea satisfies none of the above conditions.

The current widely used method of measuring IOP by applanation tonometry was developed by Goldmann based on studies on cadaver eyes in 1957. Goldmann discussed the limitations of applying the Imbert-Fick's principle to the cornea. Goldmann, V. H. Schmidt T., "Uber applanation-stonometrie," Opthalmologica 134:221–242 (1957). The wet surface of the eye creates surface tension (S), and the thickness of the wall creates a counterforce (E) against the force (W) applied on the sphere surface.

Imbert-Fick's Principle States:

$$P+E=W/A-S \qquad (1)$$

In which:
P=IOP as measured by the tonometer
E=modulus of elasticity of corneal deformation, corneal thickness being a major factor
W=the force acting on the tonometer tip
A=area of contact between the tonometer tip and flattened cornea
S=the attractive force of surface tension By measuring various variables involved, an applanation prism was designed and calibrated with a diameter of 3.06 mm assuming the corneal thickness to be 0.5 mm, thus canceling surface tension (5) and effect of the thickness of the cornea (E), simplifying the equation to $$P=W/A \qquad (2)$$

Using known or measured values of A and W, IOP is determined.

Goldmann measured the thickness of a handful of eyes in Switzerland and assumed the corneal thickness to be a constant value of half a mm. It was necessary for him to reduce variables in Imbert-Fick formula to devise his instrument. He stated in his writing that theoretically the variation in corneal thickness will affect the reading of IOP, but there is no indication he was aware of the magnitude of error caused by corneal thickness.

Goldmann was also aware of the effect of corneal curvature (K) on applanation reading. He devised the prism to be rotatable to get applanation readings in the steepest and flattest meridian of the cornea. In highly astigmatic corneas, the steeper meridian yields a higher reading. In astigmatic corneas, the area of the oval surface applanated has to be compared to the ideal round surface.

Ehlers et al of Denmark in 1975 studied the relationship between central corneal thickness (CCT) and AT in rabbits and 29 human eyes. Ehlers, H. et al., "Applanation tonometry and central corneal thickness," Acta Ophthalmol 53:34–43, (1975). Ehlers et al. measured CCT by optical means, cannulated human eyes in vivo and compared the defined IOP and AT measured with a Perkins or Draeger hand held applanation tonometer calibrated against standard Goldmann tonometer. They found statistically significant correlation between CCT and error of AT($\Delta$P). Having seen a linear relationship between the two variables in preliminary study, they calculated the intermediate pressure level from $\Delta$P 10 and $\Delta$P 30 by linear interpolation. They offered a correction table to obtain IOP from CCT and AT. They eliminated eyes with astigmatism greater than 1.5 D to avoid the errors caused by astigmatic eyes. They saw a linear relation between CCT and K in rabbit eyes but not in 29 human eyes they studied. They predicted that study in larger human sample might confirm the similar relation in humans. Over a span of 140 micron of difference in CCT, error of AT ($\Delta$P) ranged 8.7 mmHg (−4.5 to +4.2) at an AT level of 10 mmHg; it ranged 9.3 mmHg (−4.6 to +4.7) at an AT level of 15 mmHg; it ranged 9.9 mmHg (−4.7 to 5.2) at an AT level of 20 mmHg; it ranged 10.5 mmHg (−4.8 to +5.7) at an AT level of 25 mmHg and 11.1 mmHg (−4.9 to +6.2) at an AT level of 30 mmHg.

In 1995, Argus of Indiana studied CCT of 36 patients with ocular hypertension (OHT), 29 control subjects and 31 patients with glaucoma. Argus, Wash., "Ocular hypertension and central corneal thickness," Ophthalmol., 102:1810–1812 (1995). CCT of OHT was 610 micron, which was significantly greater than glaucoma (557 micron) and control (567 micron). He concluded that corneal pachymetry to be clinically helpful in estimating IOP, determining the risk of visual loss and establishing a target pressure. Using ultrasonic pachymetry, he found the average corneal thickness in 96 eyes to be 567 microns.

Stodtmeister of Germany in 1998 measured CCT in 579 patients using ultrasonic pachymetry. Stodtmeister, R., "Applanation tonometry and correction according to cornea thickness," Acta Ophthalmol Scand 76: 319–324 (1998). From the thickness obtained, the correction values for IOP were calculated. Correction values of +/−2 mmHg and above were found in 50% of the patients examined, correction value of +/−3 mmHg and above in 25%+patients, and correction value +/−4 mmHg and more in 20% of patients. He used the normal corneal thickness value of 578 micron and a linear correction formula of P=A+(578−T)/14 derived from Ehlers results, proposed by Argus.

However, a need still exists for convenient and more accurate methods and systems for obtaining corrected interocular pressure values.

SUMMARY OF THE DISCLOSURE

Currently prevalent methods of measuring IOP by AT create large errors because conventional AT is based on the wrong assumption that corneal thickness is a constant value in any eye. It has been amply demonstrated that corneal thickness and curvature are variables affecting the measurement value of AT. Based on experimental data and large scale measurement in almost 2000 eyes, the mathematical formulas to correct each measurement to arrive at more accurate IOP have been developed.

In accordance with preferred embodiments of the present invention a method is provided for determining corrected intraocular pressure from measurements made by applanation tonometry. An area A is measured by applanation tonometry in conventional fashion. Central corneal thickness T is measured, for example, by pachymetry. A corrected interocular pressure P is obtained in accordance with the relationship $$P = A + (T_o - T)/X$$

wherein $T_o$ is a median corneal thickness value and wherein X is an empirically determined error ratio which declines non-linearly with increasing A.

In accordance with other preferred embodiments, X decreases non-linearly as A increases in value. For example, X may vary from about 17 to about 11 as A varies from about 5 to about 45 mmHg. X may be conveniently determined from an exponential function of A of the form $$X = 18e^{-0.005A}.$$

In further preferred embodiments, the curvature of the cornea is measured and the value P is further corrected for corneal curvature by adding to P a correction factor C related to corneal curvature. In such a case corrected ocular pressure P is given by the equation $$P = A + (T_0 - T)/X + C$$

where P is in mm Hg, A is a Goldmann applanation reading, $T_0$ is 550 microns, and T is central corneal thickness measured by ultrasonic pachymetry in microns. the curvature correction factor C is given by the equation $$C = 0.8 \cdot (r - 7.85)$$

where r is a measured radius of the cornea in millimeters.

The corneal curvature may be measured to obtain two keratometric values K1 and K2 of an astigmatic cornea, in which case the correction factor C is given by the equation $$C = 0.8 \cdot \left[ \frac{675}{K1 + K2} - 7.85 \right]$$

where K1 and K2 are measured in diopters.

Embodiments of the present invention also include systems for determining a corrected intraocular pressure P. Such systems may include an applanation tonometer, an ultrasonic pachymetry system for measuring corneal thickness, and a keratometer for measuring corneal curvature. A data link or input keyboard is used for inputting values for an applanation measurement A, for a central cornea thickness measurement T and for a measurement related in value to the radius of curvature of the cornea. A database memory may store computational constants and/or data related to error ratio values X associated with various A values. A processor selects or calculates a value of X corresponding to a measured value of A. For example, X may be obtained from a look-up table or calculated from an equation of the form $$X = 18e^{-0.005A}.$$

The processor calculates corrected intraocular pressure P in accordance with the relationship $$P = A + (T_o - T)/X + C$$

where $T_o$ is a corneal thickness constant and C is a correction calculated by the processor from the measurement(s) of corneal curvature. The system may also include a display for displaying the results of the calculation.

The foregoing is intended to provide a convenient summary of preferred embodiments of the patent invention. However, the invention to be protected is defined by the claims.

DETAILED DESCRIPTION OF THE INVENTION

Figure 1:
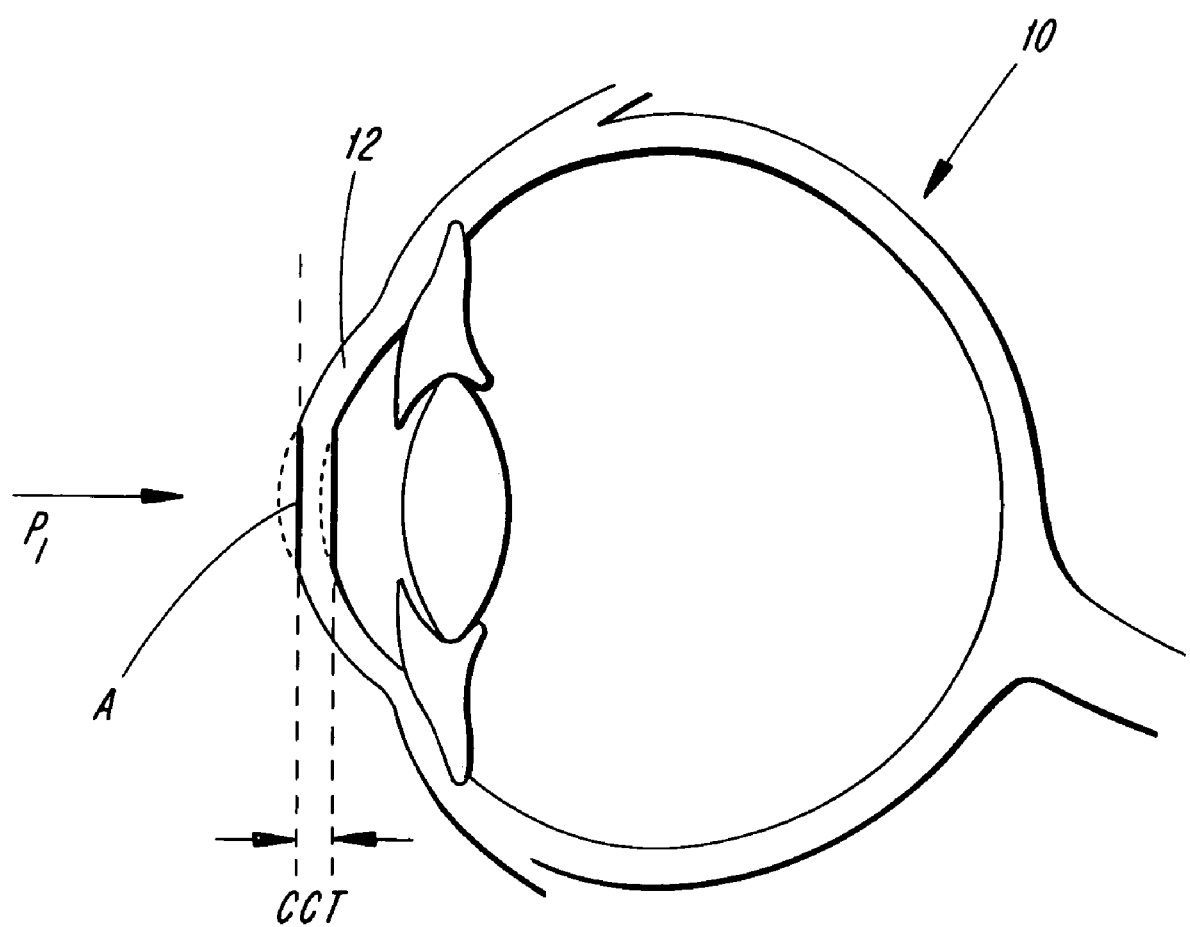
FIG. 1 is a cross-sectional view of a human eye illustrating certain aspects of measurements made and used in preferred embodiments of the present invention.

Extrapolating from data including that of Ehlers et al data, the following formulas are obtained to calculate IOP for a wide range of measurements. Ehlers measured CCT by optical means and obtained 520 micron as an average. However, based on more recent studies by pachymetry, a value of 550 micron is used as an average CCT. From this, the CCT difference from the average of 550 micrometer (550−T), T being the CCT, may be calculated.

At each level the quantity (550−T) is divided by the ratio of ΔT/ΔP, ranging between 16 to 13.3 derived from their data. Extrapolating the adjustment factors in higher and lower range yields the equation $$P = A + (550 - T)/X \qquad (1)$$

where:
P: IOP in mmHg
A: Goldmann applanation reading in mmHg
T: CCT by ultrasonic pachymetry in micron
X : ratio of the difference between I and the average $T_0$ (ΔT) over the error in

IOP(ΔP)=ΔT/ΔP

A table of values of X is presented here:

| | |
|---|---|
| X = 17 if A is 5 or 2.5 < A < 7.5 | X = −0.24A + 18.4 if 0 < A < 10 |
| X = 16 if A is 10 or 7.5 < A < 12.5; or | X = −0.20A + 18.0 if 10 < A < 20 |
| X = 15 if A is 15 or 12.5 < A < 17.5, | |
| X = 14 if A is 20 or 17.5 < A < 22.5; or | X = −0.14A + 16.8 if 20 < A < 30 |
| X = 13.3 if A is 25 or 22.5 < A < 27.5 | |
| X = 12.6 if A is 30 or 27.5 < A < 32.5; or | X = −0.12A + 16.2 if 30 < A < 40 |
| X = 12.0 if A is 35 or 32.5 < A < 37.5 | |
| X = 11.4 if A is 40 or 37.5 < A < 42.5; or | X = −0.10A + 15.4 |

$$X = 10.9 \text{ if } A \text{ is } 45 \text{ or } 42.5 < A < 47.5; \text{ or } \begin{array}{l} \text{if } 40 < A < 50 \\ X = -0.08A + 14.4 \\ \text{if } 50 < A < 60+ \end{array}$$

Alternatively, X can be calculated or described by the exponential relationship:

$$X = 18e^{-0.005A} \quad (2)$$

In an average eye with AT around 20 mmHg, a correction factor X of 14 will give reasonable correction for most applanation tonometry measurements. Above formula (1) was used to correct IOP in Applicant's patient population to compute IOP from AT and CCT. The above formula was derived from a modification of the regression formula in Ehlers' study and also Applicant's data in this study. Several tests were performed to confirm the validity of this formula against regression formulas from applicant's data, Ehler et al.'s data, Whitacre et al.'s data and Argus' data. Whitacre MM et al.: The Effect of Corneal Thickness on Applanation Tonometry. *Amer. J. Ophthalmol.*, 115:592–596, May 1993. All the regression formulas fall within a close rage. Some formulas did not take K into consideration. When regression formulas were used to calculate mean CCT value without taking K into consideration, the regression formulas yield a higher CCT value than the observed mean value of 551 microns. Applicant has observed statistically significant correlation between CCT and K in humans, but others failed to demonstrate statistically significant correlation due probably to their smaller sample sizes. Ehlers et al. also found that when IOP was corrected by CCT and K, there was a higher level of statistical significance in calculation of adjusted IOP, although the regression line between K and ΔP were not statistically significant in their study, due probably to smaller influence of K on IOP and the smaller sample size. Ehlers et al nevertheless found the relationship. Each mm of difference in corneal radius (R) causes 0.8 mmHg of error in IOP. Thus, a radius correction may be added to equation (1) as follows:

$$P = A + (550 - T)/X + 0.8 \times (r - 7.85) \quad (3)$$

where:

r: radius of curvature in mm.

Radius of curvature in mm is related to dioptric power of the cornea as follows:

$$D = (n-1)/R$$

$$\text{or, } R = (n-1)/D$$

where:

D: the dioptric power of the cornea;

n: the index of refraction of cornea=1.3375; and

R: the radius of corneal curvature in meters.

Then adjusting decimals in meters to mm, $$r = 337.5/D.$$

Formula (3) may be rewritten $$P = A + (550 - T)/X + 0.8 \cdot \left[ \frac{337.5}{D} - 7.85 \right] \quad (4)$$

Replacing D by two measured keratometric values K1 and K2 yields, $$P = A + (550 - T)/X + 0.8 \cdot \left[ \frac{675}{K1 + K2} - 7.85 \right] \quad (5)$$

where K1 and K2 are the dioptric powers of the corneal surface along the steepest and flattest perpendicular axes. For eyes with corneal astigmatism with substantial difference in curvature, LOP should be measured at steepest meridian and flattest meridian.

In accordance with the present disclosure, AT is adjusted with CCT and K values to obtain IOP using formula (5). The foregoing correction formulas were also tested in eyes which underwent keratorefractive surgery and were found to be applicable. For practical purposes of clinical tonometry, the above formulas have been found useful. For a quick calculation, formula (1) may be useful when correction for K is not necessary using a correction factor X of 14 or 15. However, for a more accurate correction taking cornea curvature into account, formulas (2) through (5) may be used. For computerized calculation of IOP from AT, CCT and K, correction factors X generated as discussed below may be used for quick and more accurate computation.

Intraocular pressure (IOP) is a physical parameter. Various natural physical forces and factors affect the pressure as discussed in connection with FIG. 1.

FIG. 1 is a cross-sectional view of the human eye 10, used to illustrate some of the involved physical forces and factors in the measurement of IOP. In applanation tonometry, a measured pressure $P_1$ is applied to the cornea 12 of the eye which produces a flattened area A. Using a Goldmann tonometer, the measured area A for a given pressure $P_1$ and IOP appears to be principally influenced by corneal thickness and curvature, although other facts such as those due to surface tension from wetting may play a part. Even temperature and gravity or altitude from sea level influence the pressure. In ordinary circumstances, the magnitude of the effects of these factors are negligible, but in extreme heat or freezing temperatures, measurable pressure changes may occur. Astronauts in zero gravity have reported changes in refractive states and IOP of their eyes in space.

In the process of devising his applanation measurement, it was necessary for Goldmann to reduce the number of variables involved and certain assumptions were necessary to eliminate variables. Tissue resiliency is also affected by rate of hydration, genetic differences in elasticity, etc. Goldmann's approach was largely theoretical and his apparatus was based on measurements in rather small numbers of 5 to 20 enucleated eyes of Swiss people, not from a large, racially diverse population. He cannulated about 20 living eyes which underwent thermal fistulization procedures to directly measure IOP at zero level only. He also used about 20 cadaver eyes to calibrate manometric values to applanation readings. He presented all the measurements in tables and no statistical analysis was performed due to rather small number of observations. He chose to regard corneal thickness as a constant of 0.5 mm to reduce one of the variables in his equations to simplify it.

The potential error associated with assuming a constant corneal thickness is illustrated by the following example. In 1977, Johnson et al. of St. Louis reported one patient with apparently benign ocular hypertension with a corneal thickness of 0.90 mm and LOP by Ta in the range of 30 to 40 mmHg. Johnson, M. et al., "Increased Corneal Thickness Simulating Elevated Intraocular Pressure," Arch. Opthalmol., 96:664, (1977). On cannulated manometry, the patient was found to have an actual IOP of 11.0 mmHg with a simultaneous Perkins applanation reading of 40.0 mmHg. These results appear anomalous. However, applying the correction formula of preferred embodiments of the present invention demonstrates consistency in the results:

$P=A+(550-T)/11.4$, $P=40+(550-900)/11.4$ $P=11$

Thus, this example illustrates the validity and usefulness of the above correction methods.

In 1993, Whitacre et al. of Kansas City did a study similar to Ehlers on 15 eyes. Whitacre, M. M. et al., "The Effect of Corneal Thickness on Applanation Tonometry," Amer J Ophthalmol 115:592–592 (1993). Whitacre et al. reported similar findings as Ehlers' with slightly less level of statistical significance probably due to their smaller sample size. Whether they eliminated eyes with higher astigmatism or not was not mentioned. Although Ehlers found Perkins' applanation was most accurate at the corneal thickness level of 520 microns, Whitacre et al. found it most accurate at corneal thickness of 540 to 550 microns when corneal thickness was measured by the overlap method of optical pachymetry. Assuming that the overlap method they used underestimates the corneal thickness by 26 to 37 microns because overlap method eliminates the thickness of tear film on corneal surface, this corneal thickness corresponds to the thickness of 560 to 580 microns when measured by the nonoverlap method. They concluded that measuring corneal thickness is necessary in properly interpreting the applanation tonometry especially in the case of thin corneas.

Measured intraocular pressure may require different correction after the eye has been altered by keratorefractive surgery. After keratorefractive surgery, corneal thickness is reduced significantly in myopic eyes, also resulting in flattening of cornea, which results in reduction in myopic or astigmatic power of the entire eye. Both CCI and K changes occur simultaneously and concomitantly resulting in the change in the AI. For example, myopic LASIK can create about 14 micron of thinning of central corneal thickness to produce 1 diopter of correction. A thinning of 140 microns of CCI in a minus 10 diopter eye creates AT reduction of 10 mmHg from loss of thickness and an AT gain of 1.25 mmHg by loss of curvature. In accordance with the formula (4) this dictates a correction (reduction). Applicant has attempted to identify instances where both effects have additive or compounding effect in changing AT. To this end, applicant studied eyes which underwent Hyperopic correction. These eyes on an average reduced CCI less than 10% on average and steepening, in varying amounts, the central cornea.

To illustrate the impact of CCT and K on IOP in clinical situations, assume a patient with AT of 20 mmHg. How is the patient to be treated? The true IOP lies somewhere between 8 and 32 mmHg. Without knowing CCT and K, one does not know the real IOP. For another example, if an African-American patient were found to have AT of 28 mmHg with deep cupping and nerve fiber thinning, with slight visual field defect, a clinician might diagnose chronic open angle glaucoma and prescribe ocular medications to reduce AT successfully to 18 mmHg level; a 36% reduction in AT. But is this an adequate therapy? A reduction in AT of 36% seems sufficient. Most clinicians would be satisfied with this treatment. However, if the visual field defect deteriorates and cupping increases rapidly, the conventional interpretation is that the deterioration is the result of the genetic predisposition of African-Americans to such fate. However, when CCT is measured to be 400 microns, true IOP may be corrected using the methods of the present invention to be 10 mmHg higher. After correction, the patient's original IOP is 38 mmHg, and it is reduced only to the level of 28 mmHg therapy. This is still too high. Thus, the common practice of setting a target by percentage reduction of unadjusted AT seems inappropriate. In an alternate target setting, even the lower target AT of 15 mmHg still seems inadequate when we know the true IOP will still be 25 mmHg.

African-Americans have thinner but relatively flatter cornea, compounding the under reading of AT. This may contribute to delay in diagnosis and inadequate target IOP setting in glaucoma therapy in African-Americans and also in normotensive and low tension glaucoma patients. Applanation tension readings were similar in all 4 ethnic groups in otherwise unselected populations which may reasonably represent the general population, but when AT was corrected for CCT and further for CCT and K, African-Americans were found to have higher IOP of statistical significance than Caucasians. This put them in disadvantage even before glaucoma is diagnosed.

Figure 2:
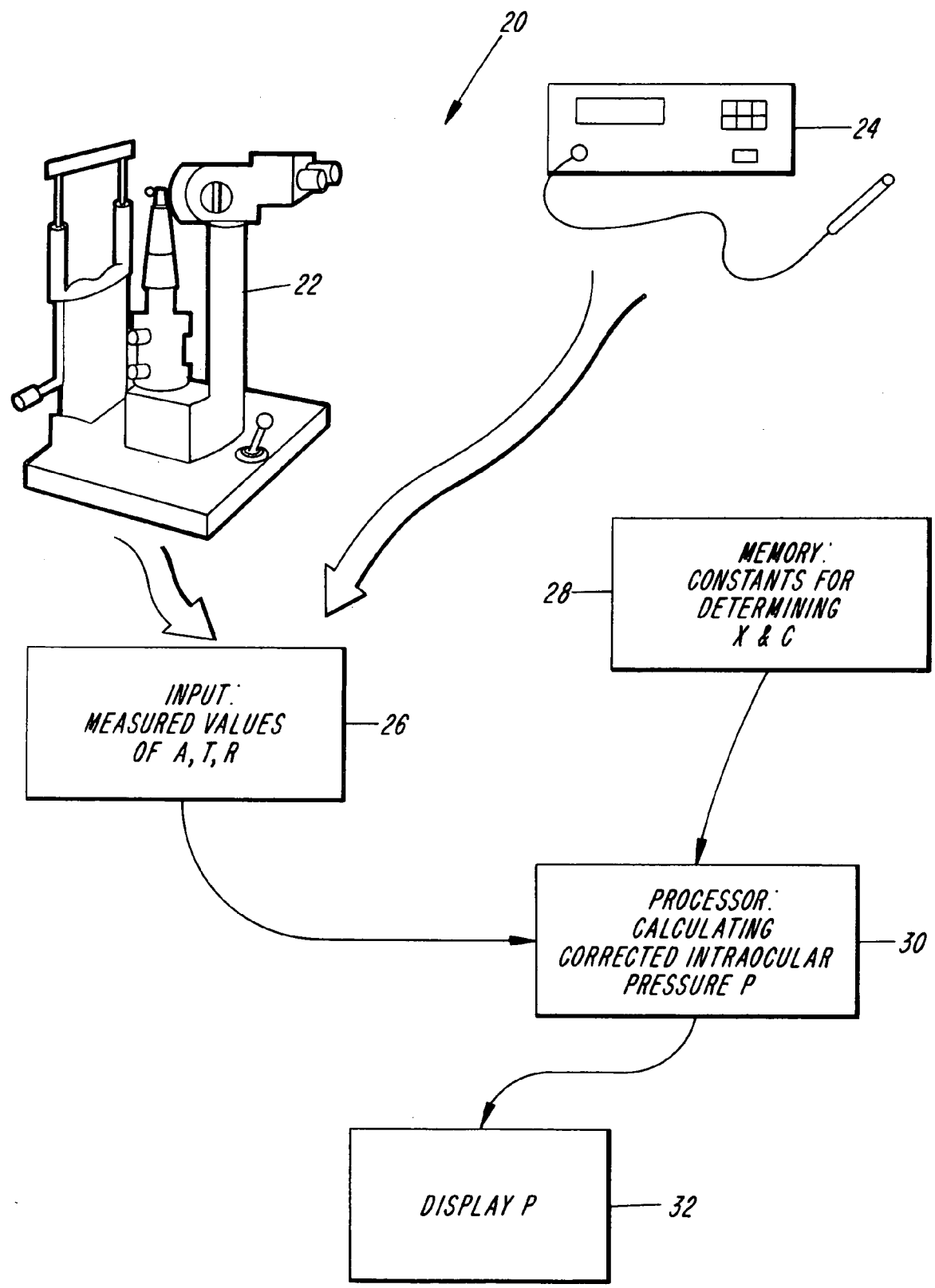
FIG. 2 is a schematic illustration of a system for determining a corrected intraocular pressure in accordance with a preferred embodiment of the present invention.

FIG. 2 illustrates a system 20 for determining a corrected intraocular pressure P. The system may include a keratometer and applanation tonometer 22 for measuring corneal curvature K and uncorrected IOP (from the measurement of flattened corneal area A). A pachymetry system such as an ultrasonic pachymetry system 24 may be employed to measure corneal thickness T. A data link or input keyboard 26 may be employed to input values for the measurements A, T and R. A database memory 28 may be used to store various constants for determining X and C as well as other values for applying the correction formulae discussed above. A processor 30 calculates corrected intraocular pressure in accordance with the above formulae. Alternatively, the processor may select an appropriate value of P from a look-up table based on the disclosed mathematical dependency on the input values of A, T, and R. The results of the determination of P may be displayed on display 32. The disclosed correction formulae may be incorporated into or employed in equipment having computational capabilities including calculators, computers and instruments for ophthalmic examinations to arrive at more accurate IOP measurement.

Applicant has presented mathematical formulae extrapolated from Ehlers' study and his own statistical data and regression formulae. These correction formulae will give more accurate IOP than unadjusted AT. Current methods of AT measurement (including the pneumatic tonometer and the handheld tonometer) need correction for optimum care of glaucoma and pressure related eye diseases. All eye examinations should include pachymetry (CCT) and keratometry (K) with AT to assist in obtaining true IOP. CCT needs to be measured once every few years.

Diagnosis and management of glaucoma may be based on knowledge of more accurate IOP values adjusted by CCT and K. After knowing more accurate IOP values, ethnicity or thin or flat cornea may be properly viewed as masking factors rather than risk factors. High, true IOP is the greatest risk factor in glaucoma. With the knowledge of a corrected IOP more nearly representative of true IOP, better diagnoses may be made and better treatment plans may be offered. The IOP correction formulae disclosed will offer more accurate IOP within an error range of about 1 mmHg.

This invention will enable healthcare professionals to more accurately determine IOP and diagnose glaucoma, true Ocular Hypertension, true Low Tension Glaucoma, etc. Accordingly, decision making and management of such patients may be based on more accurate information, not based on guesswork or erroneous measurement numbers that may confuse clinicians and lead them to an erroneous course of therapy.

While the present invention has been described with reference to preferred embodiments, these are to be regarded as illustrative rather than limiting. The invention to be protected is defined by the following claims.

I claim:

1. A method for determining and using intraocular pressure comprising:
   measuring intraocular pressure A by applanation tonometry;
   measuring central corneal thickness T by pachymetry;
   obtaining a corrected intraocular pressure P in accordance with the relationship $P=A+(T_o-T)/X$ wherein $T_o$ is a median corneal thickness value and wherein X is an empirically determined error ratio which declines in value for increasing A;
   and using the obtained intraocular pressure to diagnose a pressure-related eye disease.

2. The method of claim 1, further comprising the step of measuring the curvature of the cornea and wherein the value P is further corrected for corneal curvature by adding to P a correction factor C related to corneal curvature.

3. The method of claim 2, wherein the corrected intraocular pressure P is given by the equation $P=A+(T_o-T)/X+C$ where P is in mmHg, A is a Goldmann applanation reading, $T_o$ is 550μ (microns), and T is central corneal thickness measured by ultrasonic pachymetry in microns.

4. The method of claim 3, wherein the correction factor C is given by the equation $C=0.8 \cdot (r-7.85)$ where r is a measured radius of the cornea in millimeters.

5. The method of claim 4 wherein X is in the form of an exponential function of A.

6. The method of claim 3, wherein corneal curvature is measured to obtain two keratomeric values K1 and K2 of an astigmatic cornea and wherein the correction factor C is given by the equation:

$C = 0.8 \cdot \left[ \frac{675}{K1+K2} - 7.85 \right]$

7. The method of claim 3, wherein X is a function of A and varies from about 17 to about 11 as A varies from about 5 to about 45 mmHg.

8. The method of claim 7, wherein X is given by the equation $X=18e_{0.005A}$.

9. The method of claim 1 wherein X is a function of A and decreases nonlinearly as A increases in value.

10. The method of claim 1, wherein X varies in accordance with the following table

| A Range | X Value |
| --- | --- |
| 0 < A < 10 | X = −0.24A + 18.4 |
| 10 < A < 20 | X = −0.20A + 18 |
| 20 < A < 30 | X = −0.14A + 16.8 |
| 30 < A < 40 | X = −0.12A + 16.2 |
| 40 < A < 50 | X = −0.10A + 15.4 |
| 50 < A < 60+ | X = −0.08A + 14.4. |

11. A method for determining intraocular pressures by correcting measured pressure values, A, obtained by applanation tonometry for patients, wherein the measured A values vary between at least 10 and 40 mmHg and using an obtained intraocular pressure comprising:
   measuring intraocular pressures A by applanation tonometry of the patients;
   measuring central corneal thicknesses T by pachymetry for the patients; and
   measuring at least one radius of the curvature r of the cornea of the patients;
   obtaining a corrected intraocular pressure P for each patient in accordance with the relationship $P=A+f(T,X)+C(r)$ where X is describable as a non-linear function of measured A values, where f(T,X) is a pressure correction term expressible as a function of T and X and wherein C(r) is a pressure correction term expressible as a function of r and
   using the obtained intraocular pressure to treat a pressure-related eye disease.

12. The method of claim 11, wherein $f(T,X)=(T_o-T)/X$ wherein $T_o$ is a median corneal thickness value, and wherein $C(r)=c_1 \cdot (r-c_2)$ where $c_1$ and $c_2$ are constants.

13. The method of claim 12 wherein X is described by an exponential function of A.

14. The method of claim 12 wherein X is given by the equation $X=18e^{-0.005A}$.

15. A system for determining a corrected intraocular pressure P comprising
   means for inputting values for an applanation measurement A, for a central corneal thickness measurement T and for a measurement related in value to a radius of curvature of the cornea;
   a processor configured to obtain a value of X corresponding to a measured value of A and to calculate corrected intraQcular pressure P in accordance with the relationship $P=A+f(T,X)+C$ where f(T,X) is a correction for corneal thickness and C is a correction determined from the measurement related in value to curvature of the cornea; and
   means for displaying the results of the calculation.

16. The system of claim 15 wherein C is determined as a function of radius, dioptric power or keratometric values of the cornea.

17. The system of claim 15, further comprising a Goldmann applanation measurement device for obtaining a value A in mmHg.

18. The system of claim 15, further comprising an ultrasonic pachymetry system for measuring central corneal thickness.

19. The system of claim 15, wherein the processor calculates the corrected intraocular pressure P in accordance with the equation $$P=A+(550-T)/X+0.8(337.5/D-7.85)$$

wherein P and A are in mmHg, T is in microns, and D is a measured dioptric value of the cornea.

20. The system of claim 15, wherein the processor calculates the corrected intraocular pressure P in accordance with the equation $$P = A + \frac{550-T}{X} + 0.8 \cdot \left[\frac{675}{K1+K2} - 7.85\right]$$

where P and A are in mm Hg, T is in microns, and K1 and K2 are two measured keratometric values in diopters.

21. The system of claim 15, wherein $$f(T,X)=(T_o-T)/X$$

where $T_o$ is a median central cornea thickness for the general population as measured by a thickness measuring technique and wherein X values decrease non-linearly with increase in the value of A.

22. The system of claim 15, wherein $$f(T,X)=(T_o-T)/X$$

where $T_o$ is 550μ where T is measured in microns and wherein X values given by an equation of the form $$X=-x_1 A + x_2$$

for different ranges of measured A.

23. The system of claim 22, wherein $x_1$ varies from about 0.24 to 0.08 for A in the range 0<A<60 and wherein $x_2$ varies from about 18.4 to about 15.4 for A in the range 0<A<60.

24. The system of claim 15, wherein X values are selected from the following values from a database memory

| A Range | X Value |
| --- | --- |
| 2.5 < A < 7.5 | X = 17 |
| 7.5 < A < 12.5 | X = 16 |
| 12.5 < A < 17.5 | X = 15 |
| 17.5 < A < 22.5 | X = 14 |
| 22.5 < A < 27.5 | X = 13.3 |
| 27.5 < A < 32.5 | X = 12.6 |
| 32.5 < A < 37.5 | X = 12.0 |
| 37.5 < A < 42.5 | X = 11.4 |
| 42.5 < A < 47.5 | X = 10.9. |

25. The system of claim 15 wherein X is in accordance with the equation $$X=18e^{0.005A}.$$

26. The system of claim 19 where X is in the form of an exponential function of A.

* * * * *